United States Patent
Niemimäki

(10) Patent No.: US 9,149,213 B2
(45) Date of Patent: Oct. 6, 2015

(54) METHOD FOR CALIBRATING EXERCISE APPARATUS

(75) Inventor: Mika Niemimäki, Haukipudas (FI)

(73) Assignee: Polar Electro Oy, Kempele (FI)

( * ) Notice: Subject to any disclaimer, the term of this patent is extended or adjusted under 35 U.S.C. 154(b) by 691 days.

(21) Appl. No.: 13/418,781

(22) Filed: Mar. 13, 2012

(65) Prior Publication Data

US 2012/0253486 A1 Oct. 4, 2012

(30) Foreign Application Priority Data

Mar. 30, 2011 (FI) .................................... 20115301

(51) Int. Cl.
- *G06F 19/00* (2011.01)
- *A61B 5/11* (2006.01)
- *A61B 5/00* (2006.01)
- *G01C 22/00* (2006.01)

(52) U.S. Cl.
CPC ............... *A61B 5/1123* (2013.01); *A61B 5/112* (2013.01); *A61B 5/681* (2013.01); *G01C 22/006* (2013.01)

(58) Field of Classification Search
USPC ........................................ 702/149, 158, 160
See application file for complete search history.

(56) References Cited

U.S. PATENT DOCUMENTS

| | | | |
|---|---|---|---|
| 5,117,444 A * | 5/1992 | Sutton et al. | 377/24.2 |
| 6,145,389 A * | 11/2000 | Ebeling et al. | 73/865.4 |
| 6,876,947 B1 | 4/2005 | Darley et al. | |
| 2001/0022828 A1* | 9/2001 | Pyles | 377/24.2 |
| 2001/0032105 A1* | 10/2001 | Frye et al. | 705/7 |
| 2007/0270721 A1* | 11/2007 | Ananny et al. | 600/595 |
| 2009/0043531 A1* | 2/2009 | Kahn et al. | 702/149 |
| 2010/0010774 A1 | 1/2010 | Ma et al. | |
| 2010/0311544 A1 | 12/2010 | Robinette et al. | |
| 2011/0032105 A1* | 2/2011 | Hoffman et al. | 340/573.1 |

OTHER PUBLICATIONS

S. Mundakapadam, European Search Report for corresponding European Application No. EP1216 0458, p. 1-2, Jul. 19, 2012.
Tuomo Reiniaho, Finnish Official Action from corresponding Finnish Application No. 20115301, p. 1-2, Nov. 14, 2011.

* cited by examiner

*Primary Examiner* — Mohamed Charioui
*Assistant Examiner* — Catherine Rastovski
(74) *Attorney, Agent, or Firm* — Hoffmann & Baron, LLP

(57) ABSTRACT

A procedure for calibrating walking and/or running measurements in an exercise-related apparatus are provided. As a result of a user running and walking a given distance which may be the same or different for running and walking, respective running and walking motion metrics are obtained during a calibration phase. A relation between the obtained running and walking motion metrics are then used to compute a calibration value applied to calibrate one of running and walking measurements during an exercise.

20 Claims, 3 Drawing Sheets

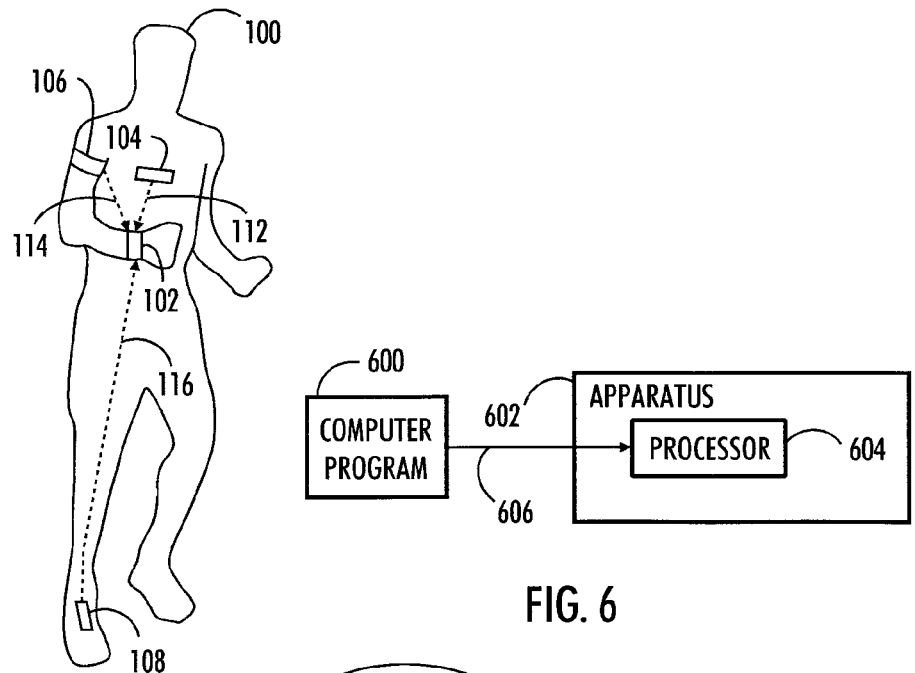
FIG. 1
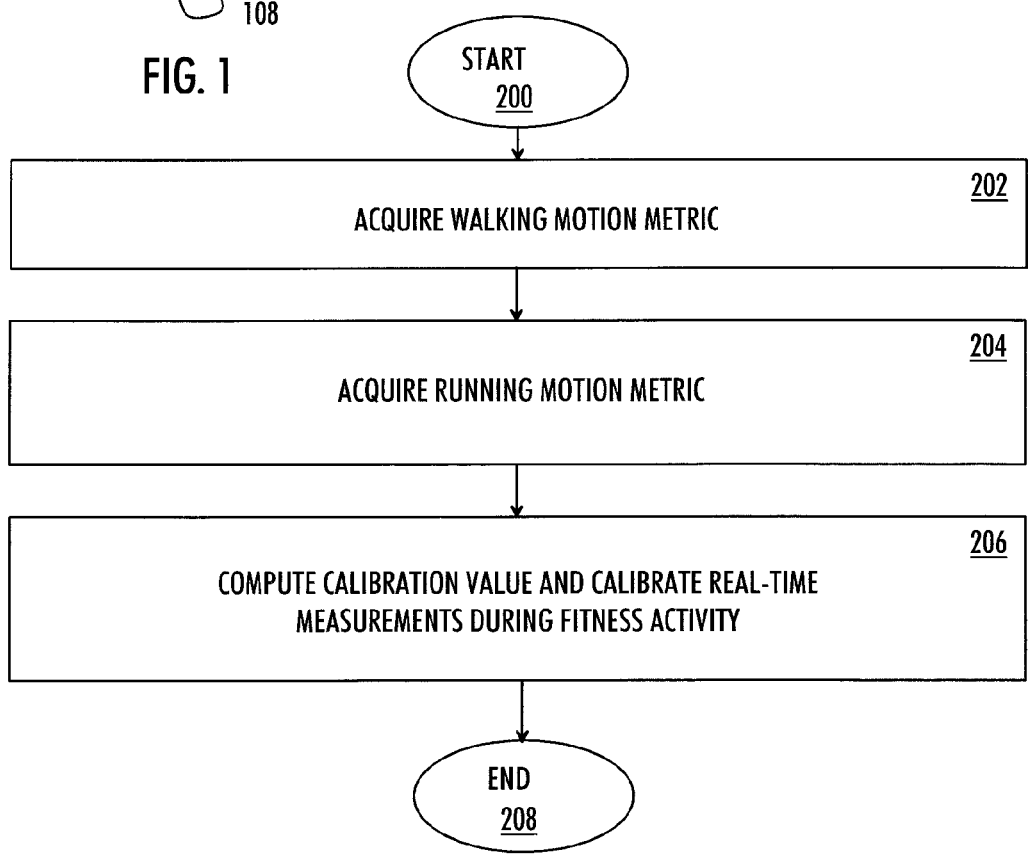
FIG. 6
FIG. 2

METHOD FOR CALIBRATING EXERCISE APPARATUS

CROSS-REFERENCE TO RELATED APPLICATION

This application claims priority based on Finnish Application No. 20115301, filed Mar. 30, 2011, which is incorporated herein by reference in its entirety.

BACKGROUND

1. Field

The invention relates to the field of sports activities and, particularly, to measuring motion.

2. Description of the Related Art

One application of motion sensors is to measure speed, distance and/or strides during an exercise or sports activity. A motion sensor may be comprised in an apparatus worn by a user, e.g. a wrist unit, chest belt or a stride sensor attached to a shoe or a belt. The same motion sensor is typically used for measuring all types of motion of the user, including walking and running. Measuring different types of motion may result in inaccuracies.

SUMMARY

According to an aspect of the present invention, there is provided an apparatus comprising at least one processor configured to cause the apparatus to: acquire, during a calibration phase, at least one walking motion metric obtained from a measured local motion of a user under a condition where the user has walked a first real distance; acquire, during the calibration phase, at least one running motion metric obtained from a measured local motion of the user under a a condition where the user has run a second real distance which may be the same as or different from the first real distance; compute a calibration value on the basis of a relation between the at least one walking motion metric and the at least one running motion metric; and calibrate one of running and walking measurements with said calibration value during an exercise phase.

According to another aspect of the present invention, there is provided an apparatus comprising: means for acquiring, during a calibration phase, at least one walking motion metric obtained from a measured local motion of a user under a condition where the user has walked a first real distance; means for acquiring, during the calibration phase, at least one running motion metric obtained from a measured local motion of the user under a condition where the user has run a second real distance which may be the same as or different from the first real distance; means for computing a calibration value on the basis of a relation between the at least one walking motion metric and the at least one running motion metric; and means for calibrating one of running and walking measurements with said calibration value during an exercise phase.

In an embodiment, the apparatus further comprises means for determining which one of the walking motion metric and the running motion metric provides less accurate measurement results; and means for calibrating the less accurate motion metric with said calibration value during the exercise phase. In an embodiment, it may be determined by default that the running motion metric is less accurate.

In an embodiment, when the second real distance is different from the first real distance, the apparatus is provided with information on relation between the first real distance and the second real distance, and wherein the apparatus further comprises means for scaling at least one of the running motion metric and the walking motion metric according to said relation in order to make the running motion metric and the walking motion metric to represent the same real distance.

In an embodiment, said at least one walking motion metric comprises time measured for the user to walk the first real distance and at least one of distance and speed measured from local motion of the user when walking the first real distance, and wherein said at least one running motion metric comprises time measured for the user to run the second real distance and at least one of distance and speed measured from local motion of the user when running the second real distance. The apparatus may further comprise means for computing a running speed calibration value by dividing a difference between a measured walking distance and a measured running distance by the time measured for the user to walk the first real distance and to calibrate, during the exercise phase, measured running speed with the speed calibration value. The apparatus may further comprise means for adding the speed calibration value to the measured running speed during the exercise phase. In another embodiment, the apparatus comprises means for dividing the speed calibration value by a measured running speed measured as a running motion metric; and means for multiplying the measured running speed during the exercise phase by thus obtained divided speed calibration value.

In an embodiment, the apparatus further comprises means for computing a running distance calibration value by dividing the difference between a measured walking distance and a measured running distance by the measured running distance; and means for calibrating, during the exercise phase, measured running distance with the running distance calibration value.

In a further embodiment, the apparatus further comprises user interface means; means for informing the user through the user interface about the start of the calibration phase; means for detecting the start of a walking stage and initiating measurement of the at least one walking motion metric; means for detecting the end of the walking stage and terminating measurement of the at least one walking motion metric; means for detecting the start of a running stage and initiating measurement of the at least one running motion metric; means for detecting the end of the running stage and terminate measurement of the at least one running motion metric; and means for informing the user through the user interface about the end of the calibration phase. The apparatus may further comprise means for instructing the user to at least one of start and end the walking stage and the running stage during the calibration phase. The apparatus may further comprise means for instructing the user to stand still at the beginning and end of the walking stage and the running stage so as to facilitate the detection of the walking stage and the running stage during the calibration phase.

In an embodiment, the apparatus further comprises means for displaying the calibrated measurement results to the user during and/or after the exercise through said user interface means.

According to yet another aspect of the present invention, there is provided a computer program product embodied on a non-transitory distribution medium readable by a computer and comprising program instructions which, when loaded into an apparatus, execute a computer process comprising: acquiring, during a calibration phase, at least one walking motion metric obtained from a measured local motion of a user under a condition where the user has walked a first real distance; acquiring, during the calibration phase, at least one running motion metric obtained from a measured local motion of the user under a condition where the user has run a second real distance which may be the same as or different from the first real distance; computing a calibration value on the basis of a relation between the at least one walking motion metric and the at least one running motion metric; and calibrating one of running and walking measurements with said calibration value during an exercise phase.

BRIEF DESCRIPTION OF THE DRAWINGS

Embodiments of the present invention are described below, by way of example only, with reference to the accompanying drawings, in which FIG. 1 illustrates an exercise-related measurement system according to an embodiment of the invention;

FIG. 2 illustrates a flow diagram of a process for calibrating measurements according to an embodiment of the invention;

FIGS. 6 to 8 illustrate embodiments of an apparatus carrying out the calibration procedure.

DETAILED DESCRIPTION

Figure 3:
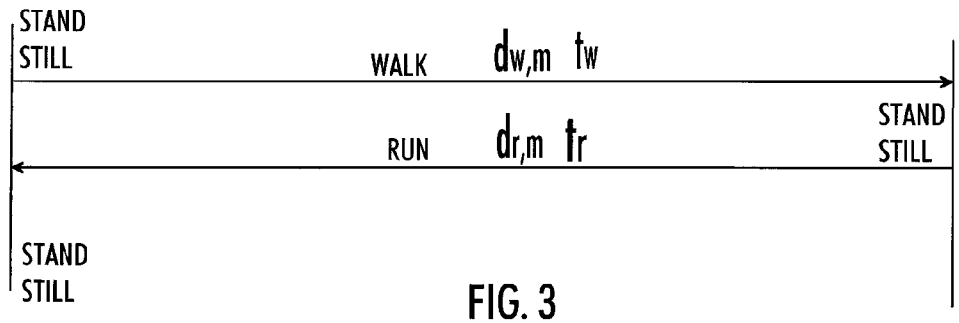
FIG. 3 illustrates the calibration procedure from a user's point of view.

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

FIG. 1 illustrates a system that may be used for carrying out measurements during an exercise or physical activity of a user 100. The system may comprise multiple portable apparatuses 102, 104, 106, 108 attached to the body of the user 100. One of the apparatuses 102 to 108 may be a user interface apparatus configured to interact with the user 100. In this example, the user interface apparatus is a wrist device 102. The wrist device 102 may be a sports computer, a running computer, a multi-sports computer, and/or an activity monitor. In other embodiments, the user interface apparatus is a subscriber terminal of a radio system (such as a mobile phone), for example. The system may further comprise at least one accessory apparatus 104 to 108 configured to measure a determined property related to the exercise or activity and to communicate with the user interface apparatus over respective wireless or wired links 112, 114, 116. An example of the accessory apparatus is a pedometer, a foot-pod, a shoe-mounted stride sensor, in general a measurement unit 108 attachable to a lower limb of the user. Another example of the accessory apparatus is a heart rate monitor for measuring the user's heart rate and possibly other physiological parameters that can be measured from the user 100. The heart rate monitor may be based on a wireless heart rate monitoring concept where a transmitter 104 attached to the user's 100 chest measures the user's 100 heart rate and transmits heart rate information telemetrically to a heart rate receiver attached to the user's wrist, e.g. the user interface apparatus. Other implementations may also be possible. The heart rate monitor may also be implemented such that the heart rate is directly measured from the wrist on the basis of pressure or optical measurement, for example. In this case, the heart rate monitor may be integrated in the wrist device 102. Other ways for measuring the heart rate may also be employed. As sensor technology becomes more integrated, less expensive, and its power consumption characteristics are improved, a sensor measuring heart activity data may also be placed in other arrangements besides the chest strap transmitter. Polar Electro is already marketing apparels which comprise integrated electrode structures. Other examples of the accessory apparatuses include a measurement device 106 that is designed to measure local motion of the user from other parts of the user's body, e.g. from the arm or waist.

In an embodiment, the system comprises the wrist device 102 that may be worn around the wrist, like a watch, and a stride sensor 108. Polar Electro Inc. designs and manufactures such apparatuses 102 and their accessories. At the time of filing this patent application, the apparatus 102 may be implemented based on a multi-sport sports computer RS800CX available from Polar Electro Inc. with the stride sensor 108, for example. The implementation of the embodiments in such an existing product requires relatively small and well-defined modifications. Naturally, as the products evolve, feasible platforms for the implementation of the embodiments described herein also evolve and emerge.

Embodiments of the invention relate to measurement of walking and running properties from local motion of the user by using the same sensor, e.g. the stride sensor 108 or another sensor attached to the user's body. Walking and running are associated with different types of local motion of the user's body and, therefore, measurements may result in inaccuracies at least with respect to one type of motion (running motion or walking motion). Therefore, an embodiment of the invention carries out a calibration procedure in which the user walks and runs a given distance (may be the same or different distance for each motion), a walking motion metric and a running motion metric is measured for walking and running, respectively, and a calibration value is then computed from at least the walking motion metric and the running motion metric. Then, during the actual exercise following the calibration procedure, at least one of running and walking measurements is calibrated by using the calibration value. FIG. 2 illustrates an embodiment of such a procedure. Referring to FIG. 2 the process starts in block 200. A triggering event for initiating the procedure may be a user input through a user interface of the user interface apparatus, or the apparatus may initiate the procedure autonomously without a specific user input. Embodiments for triggering the procedure are described in greater detail below.

In block 202, at least one walking motion metric obtained from a measured local motion of the user under a condition where the user has walked a first real distance is acquired during the calibration phase. The real distance may be known or unknown to the apparatus carrying out the procedure. In block 204, at least one running motion metric obtained from a measured local motion of the user is acquired, during the calibration phase, under a condition where the user has run a second real distance. The second real distance may be the same as or different from the first real distance, and it may also be known or unknown to the apparatus. However, at least a relation between the first and second real distance, e.g. the first real distance is half of the second real distance, may be known in order to make the measured metrics comparable. It should be noted that blocks 202 and 204 may be carried out in a reversed order.

In block 206, a calibration value is computed on the basis of a difference between the at least one walking motion metric and the at least one running motion metric, one of running and walking measurements is then calibrated with said calibration value during an exercise phase, e.g. during actual activity measurements. The process ends in block 208. The process of FIG. 2 may be carried out as a computer process defined by computer instructions of a computer program product stored on a computer-readable memory medium.

The walking motion metric and the running motion metric may be measured from the local motion of the user's body by using one or more motion sensors. Motion sensors are often used for determining person's speed and/or running/walking distance. A motion sensor can be disposed in at least one of the accessory apparatuses 104 to 108, such as the stride sensor 108 attachable to the person's foot. The motion sensor can also be integrated into the wrist device 102 or the heart rate sensor 104 attachable to the user's chest. The motion sensors are often based on accelerometers which detect instantaneous acceleration values associated with the person's local motion, such as foot, arm or body motion. The local motion excludes person's overall motion obtained from external reference, such as a satellite positioning system. However, local motion may be characterized by positioning data from a satellite positioning if the accuracy of the positioning data is accurate. The accelerometer may be 1, 2 or 3 dimensional, and a sampling rate of the acceleration values may vary from tens of Hz to hundreds of Hz. Digitized instantaneous acceleration values are processed in a digital signal processor in the sensor. The speed and distance data is typically calculated in the sensor and transmitted wirelessly to the user interface apparatus, such as the wrist device 102 or the mobile phone. The speed and distance values may be obtained any one of the following exemplary analysis methods:

a) Consideration of time signatures of the acceleration signals
b) Consideration of integrals of the acceleration signals Method a) is based on step analysis where various stride signatures, such as heel strike and/or toe-off phases, are detected, and the number of steps is calculated. The time provides with walking/running pace information, and the distance and speed can be obtained from the pace or number of steps and an assumed step length of the person (may be given as an input by the user). Thus, the distance d can be obtained from equation (1):

$$d = N_{steps} \times L_{step} \quad (1)$$

where $N_{steps}$ is the number of steps during an observation period t, and $L_{step}$ is the step length. Different step length can be applied for walking and running. Speed v may be obtained from relation $v=d/t$, where t is the observation period.

Method b) is based on acceleration values throughout the step, although time signatures may still be used. The use of integrals effectively transforms the acceleration values into speed or distance variables, which are then transformed to represent the user's overall motion. In this case, there are two options:

a. determine length of trajectory of the accelerometer by integrating twice the acceleration values and obtain step length;
b. determine speed of the sensor by integrating once the acceleration values and obtain speed directly The transformation from the local motion characterization, such as that of a foot, wrist or body motion, to the overall motion characterization requires appropriate transformation parameters. The transformation parameters are typically adjusted to appropriate values in the manufacture of the sensor based on validation studies. The statistical nature of the transformation parameters may result in a need for personal calibration for individuals whose stepping dynamics during running or walking deviates from that of the average of the population. Such a calibration for the transformation may be carried out according to any state-of-the-art calibration schemes.

Figure 4:
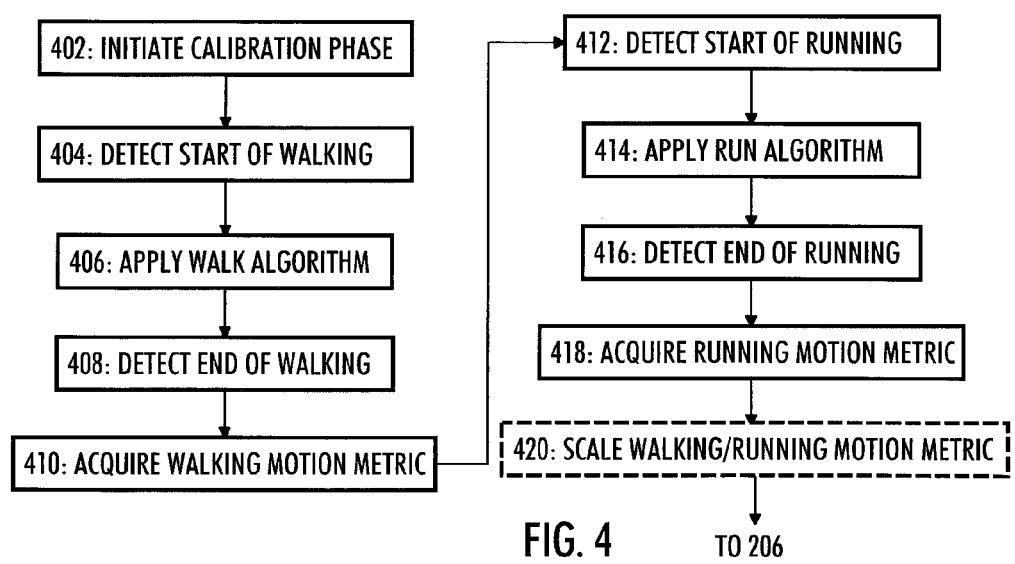
FIG. 4 illustrates the calibration procedure from point of view of an apparatus carrying out the calibration.
Figure 5:
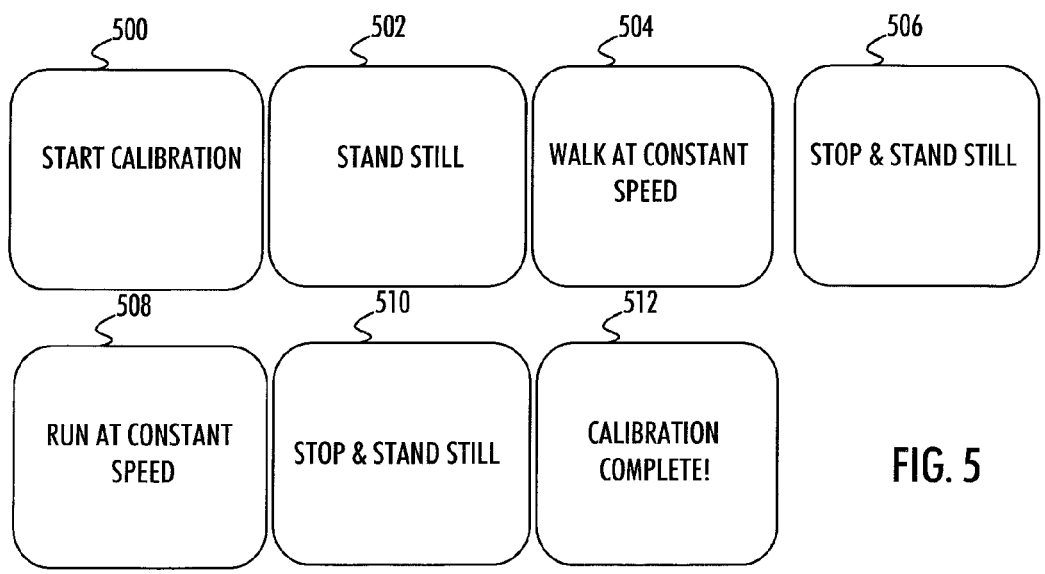
FIG. 5 illustrates interaction between the user and the apparatus during the calibration procedure.

FIGS. 3 to 5 illustrate the calibration procedure according to an embodiment of the invention from several point-of-views including the user's operation (FIG. 3), the operation of the apparatus (FIG. 4), and interaction between the apparatus and the user (FIG. 5). FIG. 3 illustrates the user's action during the calibration phase in which the user walks and runs the first and second real distance, respectively. FIG. 4 illustrates the operation of the apparatus during the calibration phase, and FIG. 5 illustrates display commands the apparatus outputs to instruct the user during the calibration through a display unit or audio interface of the user interface apparatus, e.g. the wrist device 102.

The calibration phase is initiated in block 402. The initiation may be triggered by detecting a new user operating the user interface apparatus, e.g. the wrist device 102. This may be detected by the first time operation of the user interface apparatus or by entering a new user profile in the user interface apparatus. Then, the user interface apparatus may be configured to display a command or a request to start calibration by displaying appropriate message in the display unit (see display 500 in FIG. 5). If the displayed message is associated with a request, a user input may be required to trigger the calibration.

After starting the calibration procedure, the user may be instructed (display 502) to stand still for a while, e.g. a determined time period. The determined time period may be a few seconds, e.g. three seconds, and the time period may be computed by the apparatus. In another embodiment, the apparatus may instruct the user to stand still for a while and then start movement at the user's own convenience. The stand still period may be used in order to enable the apparatus to determine a starting time for the walking phase. During the stand still period, the apparatus detects a rest stage upon acquiring of no motion data or motion data indicating minimal motion from the motion sensor(s). After the time period has expired, if the apparatus counts the time period and gives the user a command to start walking (display 504), the user starts walking at substantially constant speed. In the embodiment where the user starts the motion (walking) at his/her own will, the display 504 may be included in the display 502, or even omitted. When the user starts moving (walking), the apparatus detects a start of a walking phase in block 404. This may be detected by reception of walking related motion metrics from the motion sensor(s) or by applying a motion identification algorithm which separates different forms of motion, such as walking and running, from each other. The apparatus may also store a start time of the walking phase. The apparatus may instruct the user to walk a determined distance, to walk for a determined duration, or to walk until the apparatus instructs to stop walking. During the walking phase, the apparatus applies the walk algorithm (block 406) to measure at least one of a walking distance $d_{w,m}$ and walking speed $v_{w,m}$ that may be measured as described above. Additionally, the apparatus may determine the duration of the walking phase $t_w$. In an embodiment, the walking speed $v_{w,m}$ is an effective value, such as an average of walking speed, over the duration of the walking phase.

The end of the walking phase is detected in block 408. The detection may be based on detection of the user stopping walking and standing still on the basis of the measurements received from the motion sensor(s). The user may be instructed to stop and stand still for a while (display 506). If the start and stop of the walking phase are allowed to be determined by the user, the apparatus may be configured to verify that the walking phase was sufficiently long, e.g. by checking the duration of the walking phase $t_w$. If the duration of the walking phase $t_w$ is below a threshold, e.g. 30 seconds, the user is requested to repeat the walking phase through an appropriate display command. Upon detection of the end of the walking phase in block 408, the walking motion metric(s) $d_{w,m}$, $v_{w,m}$, $t_w$ is/are acquired in block 410.

Similarly for the running phase, the stand still phase after the walking phase may be used to enable the apparatus to determine the end of the walking phase (from the stop of the walking motion) and the start of the running phase. The user may be instructed to start running at constant speed (display 508), or the user may initiate the running autonomously. The apparatus may instruct the user to run back to the starting point of the walking phase, thus resulting in the same real distances for the running and walking. When the running is detected by the motion measurements received from the motion sensor(s) in block 412, the apparatus applies a run algorithm (block 414) to measure at least one of a running distance $d_{r,m}$ and running speed $v_{r,m}$ that may be measured as described above. Additionally, the apparatus may determine the duration of the running phase $t_r$. In an embodiment, the running speed $v_{r,m}$ is an effective value, such as an average of running speed, over the duration of the running phase.

The end of the running phase is detected in block 416. The detection may be based on detection of the user stop running and standing still on the basis of the measurements received from the motion sensor(s). The user may be instructed to stop and stand still for a while (display 510). If the start and stop of the running phase are allowed to be determined by the user, the apparatus may be configured to verify that the running phase was sufficiently long, e.g. by checking the duration of the running phase $t_r$. If the duration of the running phase $t_r$ is below a threshold, e.g. 15 seconds, the user is requested to repeat the running phase through an appropriate display command. Upon detection of the end of the running phase in block 416, the running motion metric(s) $d_{r,m}$, $v_{r,m}$, $t_r$ is/are acquired in block 418.

Thereafter, if the apparatus supports a functionality where the real walking and running distances are allowed to be different, the apparatus executes block 420 in which running or walking metrics are scaled to represent the same real distance, i.e. to make them comparable. Speed values need not be scaled, but the time/distance metrics may have to be scaled. In some embodiments, the apparatus does not implement block 420.

Then, the process proceeds to block 206 in which at least one calibration value is calculated. Next embodiments of the calibration values and how they may be calculated are described. Before calculating the calibration values, the apparatus may be configured to determine which one of the walking motion metric and the running motion metric provides less accurate measurement results and to calculate the calibration value(s) for the less accurate motion metric. In an embodiment, the apparatus determines by default that the running motion metric is less accurate. In another embodiment, the apparatus is provided with the real distance(s) walked/run by the user, and the motion metric providing less accurate measurement results with respect to the real distance is determined to be the less accurate.

With respect to calibrating the speed, let us first assume that the running speed measurements are less accurate. As a consequence, a calibration offset value $\Delta v_r$ may be computed according to the following Equation:

$$\Delta v_r = \frac{d_{w,m} - d_{r,m}}{t_r} = \frac{v_{w,m} * t_w - w_{r,m} * t_r}{t_r} \quad (2)$$

Then, the calibrated running speed may be acquired according to the following Equation:

$$v_{r,corrected} = v_{r,act} + \Delta V_r \quad (3)$$

where $v_{r,act}$ represents a running speed value measured during the exercise (after the calibration phase). In other words, the measured running speed value is offset by an added calibration offset value $\Delta v_r$.

Let us now assume that the walking speed measurements are less accurate. As a consequence, a calibration offset value $\Delta v_w$ may be computed according to the following Equation:

$$\Delta v_w = \frac{d_{r,m} - d_{w,m}}{t_w} = \frac{v_{r,m} * t_r - w_{w,m} * t_w}{t_w} \quad (4)$$

Then, the calibrated walking speed may be acquired according to the following Equation:

$$v^{w,corrected} = v_{w,act} + \Delta v_w \quad (5)$$

where $v_{w,act}$ represents a walking speed value measured during the exercise (after the calibration phase). In other words, the measured walking speed value is offset by an added calibration offset value $\Delta v_w$.

In another embodiment, a scaling factor is provided instead of the offset. With respect to calibrating the running speed, the correction may be formed instead of equation (3) as follows:

$$v_{r,corrected} = v_{r,act}(1+p) \quad (6)$$

where $$p = \frac{\Delta v_r}{v_{r,m}} \quad (7)$$

The value of p effectively defines the scaling factor 1+p scaling the measured speed $v_{r,act}$ during the exercise.

Similarly for scaling the walking speed, the correction may be formed instead of equation (5) as follows:

$$v_{w,corrected} = v_{w,act}(1+p) \quad (8)$$

where $$p = \frac{\Delta v_w}{v_{w,m}} \quad (9)$$

With respect to calibrating distance measurements, let us first assume that the running distance is less accurate. Then, a distance calibration value for the running distance may be computed as:

$$\Delta d_r = \frac{d_{w,m} - d_{r,m}}{d_{r,m}} \quad (10)$$

and the corrected running distance is acquired as:

$$d_{r,corrected} = d_{r,act}(1+\Delta d_r) \quad (11)$$

where $d_{r,act}$ represents a running distance value measured during the exercise (after the calibration phase).

Similarly for calibrating the walking distance, upon determining that it is less accurate, a distance calibration value for the walking distance may be computed as:

$$\Delta d_w = \frac{d_{r,m} - d_{w,m}}{d_{w,m}} \quad (12)$$

and the corrected running distance is acquired as:

$$d_{w,corrected} = d_{w,act}(1+\Delta d_w) \quad (13)$$

where $d_{r,act}$ represents a running distance value measured during the exercise (after the calibration phase).

In general, the difference between the running and walking motion metrics, e.g. difference between $d_{r,m}$ and $d_{w,m}$ or between $v_{r,m}$ and $v_{w,m}$, is used to determine the calibration value. After computing the calibration values according to any one or a plurality of Equations (2), (4), (7), (9), (10), and (12), the calibration phase is complete, and the completion may be notified to the user through a display message 512. Thereafter, the actual walking or running measurements may be calibrated according to any one or a plurality of Equations (3), (5), (6), (8), (11), and (13) during the exercise when exercise-related measurements are carried out.

With respect to FIG. 5, instead of using the visual messages provided as displays 500 to 512, audial messages or a combination of audial and visual messages may be provided. Preferably, at least the stop commands (506 and 510) may be provided as an audial command, e.g. a beep, as the user is currently in motion and may not be constantly monitoring the display. It should be noted that any subset of display commands of FIG. 5 may be illustrated to the user, while at least some of the commands not displayed may be provided by other means, e.g. audial messages or notifications or through a user manual.

Furthermore, with respect to the procedure described above in connection with FIGS. 3 to 5, the order of the running and walking phase may naturally be reversed, as they are independent sub-processes of the calibration phase. In an embodiment, the apparatus is not provided with pre-knowledge of the order of the running and walking phase, and the user may determine which one to carry out first. Then, in connection with blocks 404 and 416, the apparatus may execute a process in which it determines from the motion data received from the motion sensor(s) whether the current motion is associated with walking or running and, as a result, applies either the running or walking measurement algorithm.

The calibration values computed during the calibration phase apply to a determine range of walking or running speeds. When the walking or running speed used in the exercise differs greatly from the speed used in the calibration phase, the measurements become less accurate even when calibrated as described above. In order to further improve the accuracy of the measurements during the exercise, the calibration phase may be carried out separately for a plurality of running and/or walking speeds. As a consequence, a plurality of calibration values associated with different speeds is computed. Each calibration value may be associated with a determined range of running/walking speeds. During the exercise, the apparatus may be configured to select the calibration value according to the currently measured speed of the user, and maintain the current calibration value until the measured speed changes to a range associated with another calibration value and, then, the other calibration value is applied.

Figure 7:
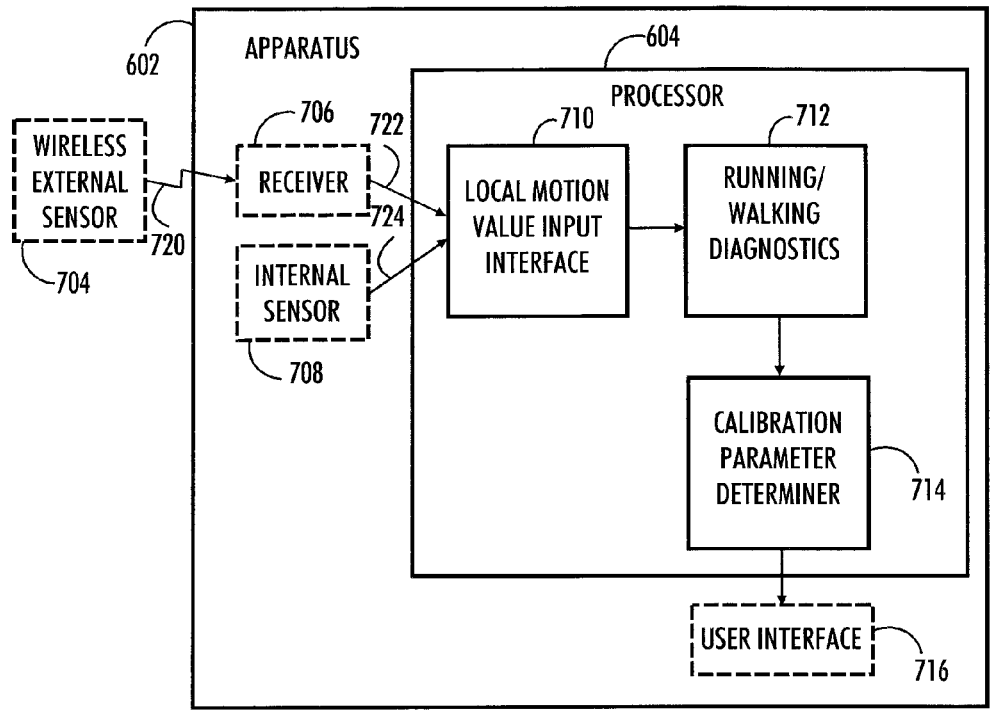
Figure 8:
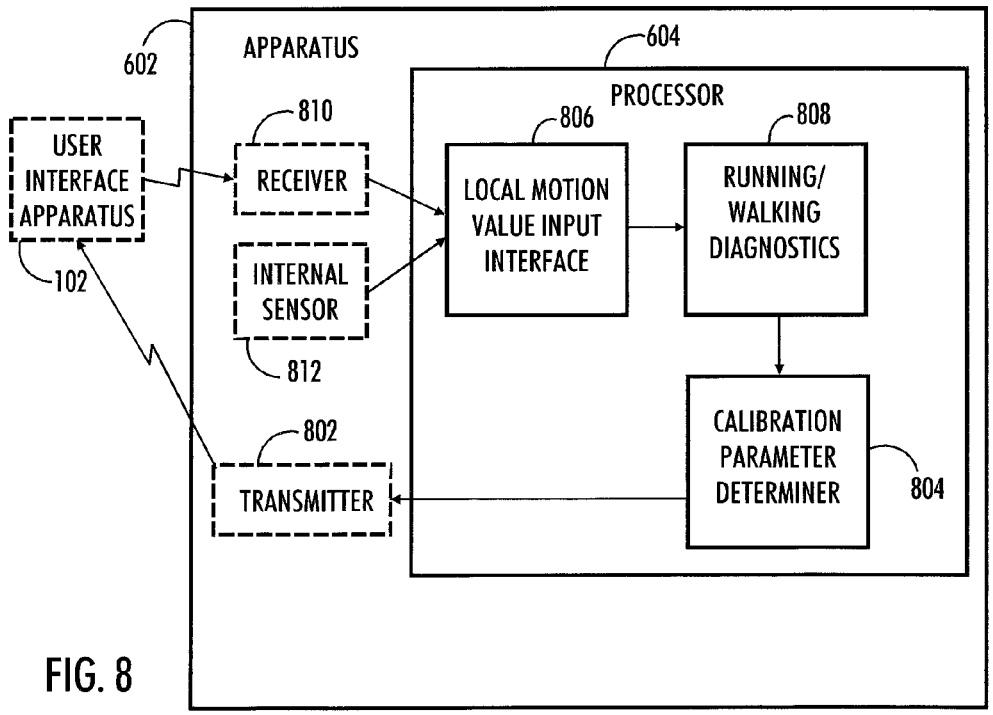

FIG. 6 illustrates an embodiment provides an apparatus 602 comprising at least one processor 604 and at least one memory 600 or at least an interface 606 to such a memory 600 that stores a computer program code. The at least one memory 600 and the computer program code are configured, with the at least one processor 604, to cause the apparatus 602 to carry out the process of FIG. 2 or any other above-described embodiment. As a consequence, the at least one memory 600 and the computer program code with the at least one processor 604 form an embodiment of means for carrying out the method of FIG. 2. FIGS. 7 and 8 illustrate embodiments of the apparatus 602. FIG. 7 illustrates an embodiment where the apparatus 602 is applicable to the user interface apparatus, and the calibration process according to embodiments of the invention is carried out in the user interface apparatus, e.g. the wrist device 102. FIG. 8 illustrates an embodiment where the apparatus 602 is applicable to the accessory apparatus, and the calibration process according to embodiments of the invention is carried out in the accessory apparatus, e.g. the stride sensor 108 or the heart rate sensor 104.

Referring to the embodiment of FIG. 7, the apparatus may acquire measured local motion data through a local motion value input interface 710. The local motion data may be acquired from an internal sensor 708 comprised in the apparatus or another apparatus disposed in the same casing as the apparatus. For example, in an embodiment where the apparatus is a processor 604 or a processing circuitry disposed in a user interface apparatus, e.g. the wrist device 102, the local motion data may be received from the internal sensor 708 that is disposed in the user interface apparatus but is external to the apparatus. In another embodiment where the apparatus is the user interface apparatus, the internal sensor 708 is comprised in the user interface apparatus. In another embodiment, the local motion data may be received over a wireless link 720 from a wireless external sensor 704 through a wireless receiver 706. The wireless external sensor 704 may be the stride sensor 108, for example. The local motion value input interface 710 may receive raw acceleration data (e.g. raw acceleration values) or processed local motion data (e.g. walking and running motion metrics $d_{r,m}$, $d_{w,m}$, $v_{r,m}$, $v_{w,m}$, $t_r$, $t_w$) from the receiver 706 over a first connection 722 or from the internal sensor 724 over a second connection 724 and forward the received local motion data to a running/walking diagnostics circuitry 712.

The diagnostics circuitry 712 may have different configurations based on the type of data received through the local motion value input interface 710. For example, if the motion data received through the local motion value input interface 710 comprises raw acceleration data, the diagnostics circuitry 712 may be configured to determine from the received acceleration data whether the data relates to running or walking motion and computes the walking/running motion metric(s) accordingly. If the data received through the local motion value input interface 710 comprises some of the needed walking/running motion metrics, e.g. $d_{r,m}$, $d_{w,m}$, $v_{r,m}$, $v_{w,m}$, the diagnostic circuitry 712 may be configured to compute the remaining walking/running motion metrics needed, e.g. $t_r$, $t_w$. If the data received through the local motion value input interface 710 comprises all the necessary walking/running motion metrics, the diagnostics circuitry 712 may be bypassed or even excluded from the apparatus 602.

The walking/running motion metrics $d_{r,m}$, $d_{w,m}$, $v_{r,m}$, $v_{w,m}$, $t_r$, $t_w$ are then applied to a calibration parameter determiner circuitry 714 configured to compute the calibration value(s) that are used to calibrate the real-time measurements during the exercise or activity. The calibration value(s) may be computed as described above. Additionally, the calibration parameter determiner circuitry 714 may carry out the actual calibration after the calibration phase by scaling or offsetting the actual measurements with the calibration value(s). The calibrated measurement results may then be output to a user interface 716 arranged to display the calibrated measurement results to the user. The user interface may be comprised in the same casing with the apparatus, or it may be an external user interface, e.g. a personal computer.

Referring to FIG. 8, this apparatus 602 applicable to the accessory apparatus, e.g. the stride sensor 108, may acquire measured local motion data through a local motion value input interface 806. The local motion data may be acquired from an internal sensor 812 comprised in the apparatus or another apparatus disposed in the same casing as the apparatus. For example, in an embodiment where the apparatus is a processor 604 or a processing circuitry disposed in the accessory apparatus, e.g. the stride sensor 108, the local motion data may be received from the internal sensor 812 that is disposed in the accessory apparatus but is external to the apparatus (the processor 604). In another embodiment where the apparatus is the accessory apparatus, the internal sensor 812 may be comprised in the accessory apparatus. The local motion value input interface 806 may receive raw acceleration data (e.g. raw acceleration values) and forward the received local motion data to a running/walking diagnostics circuitry 808. The apparatus may comprise or be connected to a receiver circuitry 810 providing a communication link with the user interface apparatus 102 so as to receive control commands from the user interface apparatus 102. As an example of commands, the user interface apparatus 102 may control the initiation of the operation of the apparatus, e.g. to start the measurements. Additionally, the user interface apparatus may trigger the apparatus to start the calibration phase. In another embodiment, the initiation of the calibration phase may be triggered by a user interface of the accessory apparatus, e.g. by the user pressing a button of the accessory apparatus.

The diagnostics circuitry 808 may have different configurations as how to process the measurement data received through the local motion value input interface 806. For example, the diagnostics circuitry 808 may be configured to determine from the received raw acceleration data whether the data relates to running or walking motion and to compute the walking/running motion metric(s) accordingly. The diagnostics circuitry 808 may be configured to compute at least some of the needed walking/running motion metrics, e.g. $d_{r,m}$, $d_{w,m}$, $v_{r,m}$, $v_{w,m}$. In another embodiment, the diagnostics circuitry 808 is configured to compute all the necessary running/walking motion metrics, e.g. $d_{r,m}$, $d_{w,m}$, $v_{r,m}$, $v_{w,m}$, $t_r$, $t_w$.

The walking/running motion metrics $d_{r,m}$, $d_{w,m}$, $V_{r,m}$, $V_{w,m}$, $t_r$, $t_w$ may then be applied to a calibration parameter determiner circuitry 804 configured to compute the calibration value(s) that are used to calibrate the real-time measurements during the exercise or activity. The calibration value(s) may be computed as described above. Additionally, the calibration parameter determiner circuitry 804 may carry out the actual calibration after the calibration phase by scaling or offsetting the actual measurements with the calibration value(s). The calibrated measurement results may then be output to a transmitter circuitry 802 configured to provide the accessory apparatus with a communication link with the user interface apparatus 102 for transmitting measured motion data to the user interface apparatus. Depending on the configuration, the apparatus may be configured to transmit raw measurement data, e.g. acceleration data to the user interface apparatus. In such a case, the calibration parameter determiner circuitry 804 and even the diagnostics circuitry 808 may be bypassed or even excluded from the apparatus. In an embodiment where the apparatus is configured to process the raw measurement data, the diagnostics circuitry 808 may be configured to process the raw acceleration data into the running/walking motion metrics or to an intermediate form from which the running/walking motion metrics may be determined in the user interface apparatus 102. In such a case, the calibration parameter determiner circuitry 804 may also be bypassed, and the diagnostics circuitry 808 may output the motion data directly to the transmitter circuitry 802.

The wireless link between the user interface apparatus 102 and the accessory apparatus 108 may be based on any one of the following wireless communication schemes: BLUETOOTH® such as BLUETOOTH® Low Energy Technology, ANT® communication originally introduced by Dynastream Innovations Inc., ZIGBEE® communication based on IEEE 802.15.4 standard or its derivative, WiFi communications based on IEEE 802.1 1x standard, and inductive transmission technology. Communication circuitries 706, 810, 802 may all be configured to support the same wireless communication scheme(s) so as to enable compatible communications between the user interface apparatus 102 and the accessory apparatus 108.

As used in this application, the term 'circuitry' refers to all of the following: (a) hardware-only circuit implementations, such as implementations in only analog and/or digital circuitry, and (b) to combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) to circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular element, a baseband integrated circuit or applications processor integrated circuit for a mobile phone or a similar integrated circuit in server, a cellular network device, or other network device.

The processes or methods described in FIGS. 2 and 4 may also be carried out in the form of a computer process defined by a computer program. The computer program may be in source code form, object code form, or in some intermediate form, and it may be stored in some sort of carrier, which may be any entity or device capable of carrying the program. Such carriers include a record medium, computer memory, read-only memory, electrical carrier signal, telecommunications signal, and software distribution package, for example. Depending on the processing power needed, the computer program may be executed in a single electronic digital processing unit or it may be distributed amongst a number of processing units.

It is evident to a person skilled in the art that, as technology advances, the inventive concept can be implemented in various ways. The invention and its embodiments are not limited to the examples described above but may vary within the scope of the claims.

What is claimed is:

1. An apparatus comprising:
a processor, the processor performing operations comprising;
computing, during a calibration phase, at least one walking motion metric obtained from a measured local motion of a user under a condition where the user has walked a first real distance, wherein the at least one walking motion metric comprises an estimated walking distance value computed by employing a walking motion algorithm during the condition, wherein the estimated walking distance value represents an estimate of the first real distance acquired by employing the walking motion algorithm;
computing, during the calibration phase, at least one running motion metric obtained from a measured local motion of the user under a condition where the user has run a second real distance which may be the same as or different from the first real distance, wherein the at least one running motion metric comprises an estimated running distance value computed by employing a running motion algorithm during the condition, wherein the estimated running distance value represents an estimate of the second real distance acquired by employing the running motion algorithm;
computing a calibration value for one of running measurements and walking measurements on the basis of both the estimated running distance value and the estimated walking distance value by using a relationship between the estimated walking distance value and the estimated running distance value; and
calibrating, using the calibration value, at least one of running and walking measurements during an exercise phase, thereby decreasing inaccurary of the apparatus in its determination of at least one of the running and walking measurements during the exercise phase without requiring entry of a predetermined distance and use of and existing calibration model during the calibration phase.

2. The apparatus of claim 1, wherein the operations further comprise:
determining which one of the walking motion metric and the running motion metric provides less accurate measurement results; and
calibrating the less accurate motion metric with said calibration value during the exercise phase.

3. The apparatus of claim 2, wherein the further comprise determining by default that the running motion metric is less accurate.

4. The apparatus of claim 1, wherein when the second real distance is different from the first real distance, the apparatus is provided with information on relation between the first real distance and the second real distance, and wherein the operations further comprise scaling at least one of the running motion metric and the walking motion metric according to said relation in order to make the running motion metric and the walking motion metric represent the same real distance.

5. The apparatus of claim 1, wherein said at least one walking motion metric comprises time measured for the user to walk the first real distance and at least one of measured walking distance and measured walking speed measured from local motion of the user when walking the first real distance, and wherein said at least one running motion metric comprises time measured for the user to run the second real distance and at least one of measured running distance and measured running speed measured from local motion of the user when running the second real distance.

6. The apparatus of claim 5, wherein the operations further comprise:
computing a running speed calibration value by dividing a difference between the measured walking distance and the measured running distance, by the time measured for the user to walk the first real distance; and
calibrating, during the exercise phase, measured running speed with the running speed calibration value.

7. The apparatus of claim 6, wherein the operations further comprise adding the running speed calibration value to the measured running speed during the exercise phase.

8. The apparatus of claim 6, wherein the operations further comprise:
dividing the running speed calibration value by a measured running speed measured as the at least one running motion metric; and
multiplying the measured running speed during the exercise phase by thus obtained divided speed calibration value.

9. The apparatus of claim 5, wherein the operations further comprise:
computing a running distance calibration value by dividing a difference between the measured walking distance and the measured running distance by the measured running distance; and
calibrating, during the exercise phase, measured running distance with the running distance calibration value.

10. The apparatus of claim 1, wherein the apparatus further comprises a user interface, and wherein the operations further comprise, during the calibration phase:
informing the user through the user interface about the start of the calibration phase;
detecting the start of a walking stage and initiate measurement of the at least one walking motion metric;
detecting the end of the walking stage and terminate measurement of the at least one walking motion metric;
detecting the start of a running stage and initiate measurement of the at least one running motion metric;
detecting the end of the running stage and terminate measurement of the at least one running motion metric; and
informing the user through the user interface about the end of the calibration phase.

11. The apparatus of claim 10, wherein the operations further comprise instructing, during the calibration phase, the user to at least one of start and end the walking stage and the running stage.

12. The apparatus of claim 10, wherein the operations futher comprise instructing, during the calibration phase, the user to stand still at the beginning and end of the walking stage and the running stage to facilitate detection of the walking stage and the running stage.

13. The apparatus of claim 1, wherein the operations further comprise displaying the calibrated measurement results to the user of during and after the exercise through a user interface.

14. A non-transitory computer-readable medium comprising instructions that, when executed by a processing device, cause the processing device to perform a method comprising:
computing during a calibration phase, at least one walking motion metric obtained from a measured local motion of a user under a condition where the user has walked a first real distance, wherein the at least one walking motion metric comprises an estimated walking distance value computed by employing a walking motion algorithm during the condition, wherein the estimated walking distance value represents an estimate of the first real distance acquired by employing the walking motion algorithm;

computing during the calibration phase, at least one running motion metric obtained from a measured local motion of the user under a condition where the user has run a second real distance which may be the same as or different from the first real distance, wherein the at least one running motion metric comprises an estimated running distance value computed by employing a running motion algorithm during the condition, wherein the estimated running distance value represents an estimate of the second real distance acquired by employing the running motion algorithm;

computing a calibration value for one running measurements and walking measurements on the basis of both the estimated running distance value the estimated walking distance value by using a relationship between the estimated walking distance value and the estimated running distance value; and calibrating, using the calibration value, at least one of running and walking measurements during an exercise phase,thereby decreasing inaccuracy of the processing device in its determination of at least one of the running and walking measurments during the exercise phase without requiring entry of a predetermined distance and use of an existing calibration model during the calibration phase.

15. An apparatus comprising:

diagnostics circuitry, the diagnostics circuitry computing, during a calibration phase, at least one walking motion metric obtained from a measured local motion of a user under a condition where the user has walked a first real distance, wherein the at least one walking motion metric comprises an estimated walking distance value computed by employing a walking motion algorithm during the condition, wherein the estimated walking distance value represents an estimate of the first real distance acquired by employing the walking motion algorithm, the diagnostics circuitry computing during the calibration phase, at least one running motion metric obtained from a measured local motion of the user under a condition where the user has run a second real distance which may be the same as or different from the first real distance, wherein the at least one running motion metric comprises an estimated running distance value computed by employing a running motion algorithm during the condition, wherein the estimated running distance value represents an estimate of the second real distance acquired by employing the running motion algorithm; and calibration parameter determiner circuitry, the calibration parameter determiner circuitry determining a calibration value for one fo running measurement and walking measurements on the basis of both the estimated running distance value and estimted walkinq distance value by using a relationship between the estimated walking distance value and the estimated running distance value, the calibration parameter determiner circuitry calibrating, using the calibration value, at least one of running and walking measurements during an exercise phase, thereby decreasing inaccuracy of the processing device in its determination of at least one of the running and walking measurements during the exercise phase without requiring entry of a predetermined distance and use of an existing calibration model during the calibration phase.

16. The apparatus of claim 15, wherein the diagnostics circuitry causes the apparatus to determine which one of the walking motion metric and the running motion metric provides less accurate measurement results and the calibration parameter determiner circuitry calibrates the less accurate motion metric with said calibration value during the exercise phase.

17. The apparatus of claim 16, wherein the calibration parameter determiner circuitry causes the apparatus to determine by default that the running motion metric is less accurate.

18. The apparatus of claim 15, wherein when the second real distance is different from the first real distance, the apparatus is provided with information on relation between the first real distance and the second real distance, and wherein the diagnostics circuitry causes the apparatus to scale at least one of the running motion metric and the walking motion metric according to said relation in order to make the running motion metric and the walking motion metric to represent the same real distance.

19. The apparatus of claim 15, wherein said at least one walking motion metric comprises time measured for the user to walk the first real distance and at least one of measured walking distance and measured walking speed measured from local motion of the user when walking the first real distance, and wherein said at least one running motion metric comprises time measured for the user to run the second real distance and at least one of measured running distance and measured running speed measured from local motion of the user when running the second real distance.

20. The apparatus of claim 19, wherein the calibration parameter determiner circuitry causes the apparatus to compute a running speed calibration value by dividing a difference between the measured walking distance and the measured running distance by the time measured for the user to walk the first real distance and to calibrate, during the exercise phase, measured running speed with the running speed calibration value.

* * * * *